(12) United States Patent
Shin et al.

(10) Patent No.: US 7,280,233 B2
(45) Date of Patent: Oct. 9, 2007

(54) METHOD AND APPARATUS FOR INSPECTING AN EDGE EXPOSURE AREA OF A WAFER

(75) Inventors: Koung-Su Shin, Suwon (KR); Sun-Yong Choi, Sungnam (KR); Chung-Sam Jun, Suwon (KR); Dong-Chun Lee, Hwasung-gun (KR); Kwang-Jun Yoon, Yongin (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 400 days.

(21) Appl. No.: 10/787,765

(22) Filed: Feb. 27, 2004

(65) Prior Publication Data
US 2004/0169869 A1  Sep. 2, 2004

(30) Foreign Application Priority Data
Feb. 28, 2003  (KR)  ...................... 10-2003-0012791

(51) Int. Cl.
 G01B 11/02 (2006.01)
 G01B 11/14 (2006.01)
 G01B 11/28 (2006.01)
 G01N 21/00 (2006.01)

(52) U.S. Cl. ...................... 356/635; 356/445; 356/614; 356/630

(58) Field of Classification Search ...................... None
See application file for complete search history.

(56) References Cited

U.S. PATENT DOCUMENTS

| | | | |
|---|---|---|---|
| 4,260,883 A * | 4/1981 | Onoda et al. ............... 250/226 |
| 5,811,211 A * | 9/1998 | Tanaka et al. ................ 430/30 |
| 5,917,588 A | 6/1999 | Addiego ..................... 356/237 |
| 6,215,551 B1 | 4/2001 | Nikoonahad et al. ....... 356/237 |
| 7,012,702 B2 * | 3/2006 | Fujiwara et al. ............ 356/614 |

FOREIGN PATENT DOCUMENTS

| JP | 2000-207562 | 2/2000 |
|---|---|---|
| KR | 10-2001-0092282 | 10/2001 |
| KR | 10-2003-0006828 | 1/2003 |
| KR | 10-2003-0010047 | 2/2003 |

* cited by examiner

Primary Examiner—Gregory J. Toatley, Jr.
Assistant Examiner—Gordon J Stock, Jr.
(74) Attorney, Agent, or Firm—Lee & Morse, P.C.

(57) ABSTRACT

For an automatic defect inspection of an edge exposure area of a wafer, an optical unit supplies a light beam onto the edge portion of a wafer and a detection unit detects light reflected from the edge portion. The detection unit converts the detected light into an electrical signal to transmit the electrical signal to a processing unit. The processing unit analyzes the electrical signal to measure the reflectivity of the edge portion, compares the measured reflectivity with a reference reflectivity, and calculates the width of the edge exposure area. The processing unit compares the calculated width with a reference width to detect any defect in the edge exposure area.

21 Claims, 3 Drawing Sheets

METHOD AND APPARATUS FOR INSPECTING AN EDGE EXPOSURE AREA OF A WAFER

BACKGROUND OF THE INVENTION

1. Field of the Invention

The present invention relates to a method and an apparatus for inspecting an edge exposure area of a wafer, more particularly to a method and an apparatus for measuring a width between an edge of the wafer and an edge of a photoresist layer formed on the wafer.

2. Description of the Related Art

Generally, semiconductor devices are manufactured by performing a fabrication process for forming an electric circuit on a silicon wafer which is used as a semiconductor substrate, an electrical die sorting (EDS) process for inspecting electrical characteristics of the semiconductor devices, and a package process for sealing and individualizing the semiconductor devices with epoxy resin.

The fabrication process includes a deposition process for forming a film on the semiconductor substrate, a chemical mechanical polishing (CMP) process for planarizing the film, a photolithography process for forming a photoresist pattern on the film, an etching process for patterning the film using the photoresist pattern in order to give electrical properties, an ion implantation process for implanting ions into predetermined portions of the semiconductor substrate, a cleaning process for removing impurities on the semiconductor substrate, and an inspection process for detecting a defect of the semiconductor substrate having the film and the pattern.

The photoresist pattern formed by the photolithography process is inspected using a microscopic inspection process before performing the etching process. In the microscope inspection process, a microscope is employed to inspect any defects of the photoresist pattern and to inspect an edge exposure area adjacent to the edge portion of the semiconductor substrate.

The edge portion of the photoresist layer formed on the semiconductor substrate is removed during an edge exposure process, e.g., using an ultraviolet ray and a developing solution. The edge exposure area indicates a ring shaped area between the edge of the wafer and the edge of the photoresist layer.

The process for inspecting the edge exposure area using the microscope is performed in order to inspect the width of the edge exposure area. However, results of the process for inspecting the edge exposure area are highly dependent on the skill of a person performing the inspection, reducing the reliability and reproducibility of the results. Further, the wafer may be contaminated when handled by a human.

In order to solve the above-mentioned problems, an apparatus having an imaging component for inspecting the edge exposure area has been developed. The imaging component can obtain the image of the edge portion of the wafer, analyze the image, and calculate the width of the edge exposure area. Because the image is obtained by the light scattered from the edge portion of the wafer, it is difficult to detect the position of the edge of the photoresist layer. Accordingly, when the edge exposure area where various films and patterns are formed is inspected using a conventional apparatus, the process for inspecting the edge exposure area may still not be sufficiently reliable.

SUMMARY OF THE INVENTION

It is a feature of the present invention to provide a highly reliable method for inspecting the edge exposure area of a wafer.

It is another feature of the present invention to provide an apparatus for inspecting the edge exposure area of a wafer.

At least one of the above and other features may be realized by providing a method including directing light onto an edge portion of a wafer, and measuring a reflectivity of the light reflected from the edge portion of the wafer. Then, the measured reflectivity is compared with a reference reflectivity to calculate a width of the edge exposure area of the wafer At least one of the above and other features may be realized by providing an apparatus for inspecting an edge exposure area of a wafer including an optical unit for irradiating a light beam onto an edge portion of the wafer, a detection unit for detecting a light reflected from the edge portion of the wafer, and a processing unit for measuring a reflectivity of the edge portion of the wafer using the light detected in the detection unit and comparing the measured reflectivity with a reference reflectivity to calculate a width of the edge exposure area of the wafer. The processing unit may compare the measured reflectivity with the reference reflectivity to detect a position of the edge of the photoresist layer formed on the wafer, and calculates the width between the edge of the wafer and the edge of the photoresist layer. The processing unit compares the calculated width of the edge exposure area with the reference width to detect any defects of the edge exposure area of the wafer.

For either the apparatus or the method, the following variations may be realized. The light may be directed over the edge portion of the wafer by rotating the wafer and irradiating the light onto the edge portion of the rotating wafer. The irradiating may further include providing the light vertically incident onto the edge portion of the wafer.

An image of the edge portion of the wafer may be obtained using the reflected light and displaying the image. The light may be expanded such that a width of the light incident on the edge portion of the wafer is larger than the edge portion of the wafer. The irradiating may further include providing light having a wavelength outside a wavelength range to which material in the edge portion is sensitive.

The measured reflectivity may be compared with the reference reflectivity to detect a position of an edge of a photoresist layer formed on the wafer and calculating the width between the edge of the wafer and the edge of the photoresist layer. The calculated width of the edge exposure area may be compared with a reference width to detect a defect of the edge exposure area of the wafer.

Because the reflectivity varies in accordance with the various films and the photoresist layer formed on the wafer, the process for inspecting the edge exposure area may be automatically performed using the apparatus when various films and patterns are formed on the wafer or one layer is formed on the wafer.

BRIEF DESCRIPTION OF THE DRAWINGS

The above and other features and advantages of the present invention will become readily apparent by reference to the following detailed description when considered in conjunction with the accompanying drawings, in which.

DETAILED DESCRIPTION OF THE INVENTION

Korean Patent Application No. 2003-12791, filed on Feb. 28, 2003, entitled "Method and Apparatus for Inspecting an Edge Exposure Area of a Wafer," is hereby incorporated by reference in its entirety.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. The relative thickness of layers in the illustrations may be exaggerated for purposes of describing the present invention.

Figure 1:
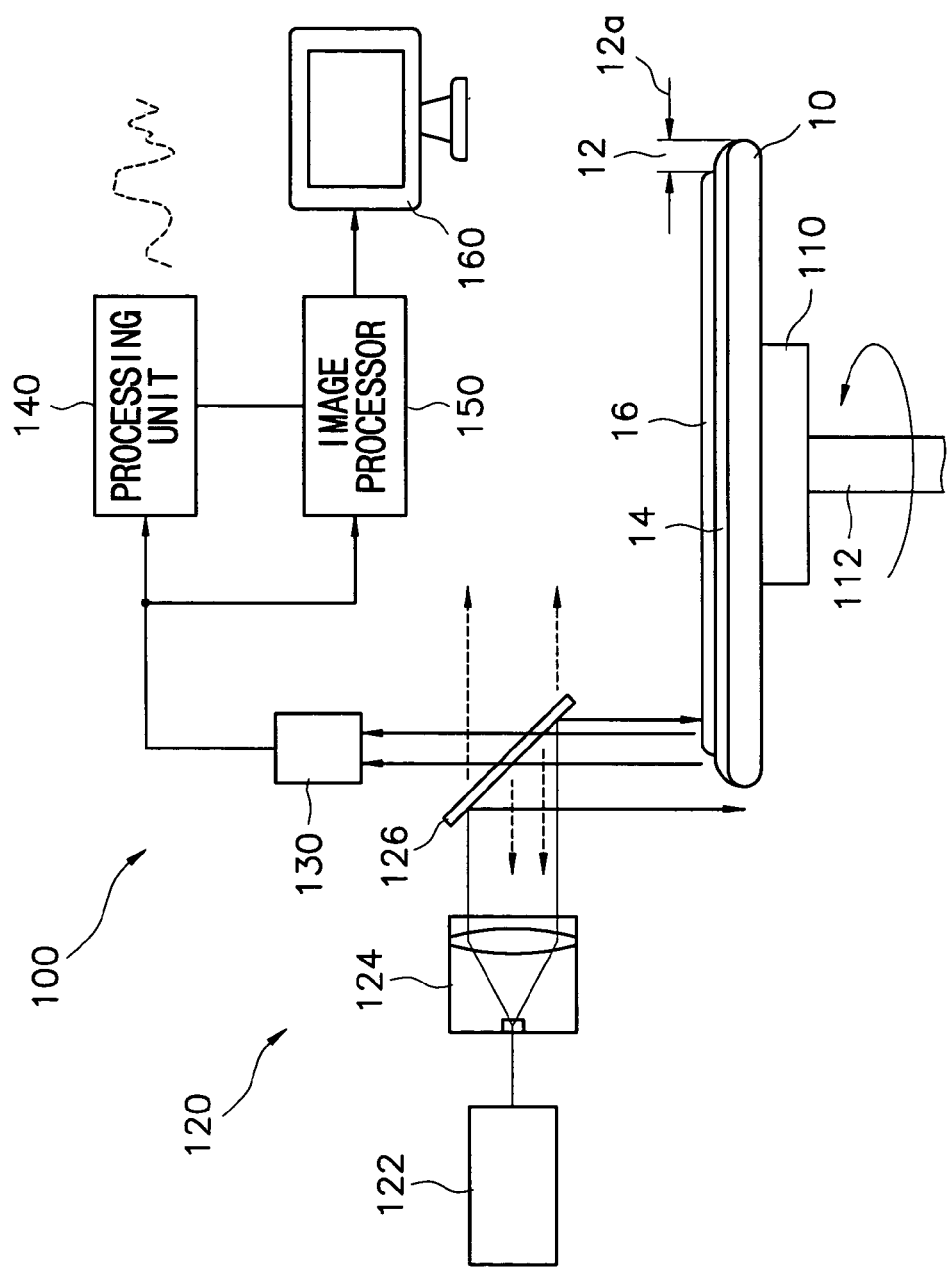
FIG. 1 is a schematic cross-sectional view illustrating an apparatus for inspecting the edge exposure area of a wafer according to one embodiment of the present invention.

FIG. 1 is a schematic cross-sectional view illustrating an apparatus for inspecting the edge exposure area of a wafer according to one embodiment of the present invention.

Referring to FIG. 1, an apparatus 100 for inspecting the edge exposure area of the wafer includes a rotation chuck 110, an optical unit 120, a detection unit 130, a processing unit 140, an image processor 150 and a display unit 160.

The optical unit 120 includes a light source 122, a beam expansion member 124 and a deflection member 126. The light source 122 may be a laser, the beam expansion member 124 may be a lens and the deflection member 126 may be a beam splitter.

The rotation chuck 110 supports a wafer 10 in a horizontal direction and rotates the wafer 10. A rotation axis 112 for delivering a rotational force to the wafer 10 is coupled to the rotation chuck 110, and a driving member (not shown) such as a motor is connected to the rotation axis 112. A vacuum channel (not shown) for providing vacuum to fix the wafer 10 is formed on the rotation chuck 110, and the vacuum channel is connected to a vacuum line formed through the rotational axis 112.

The wafer 10 may include a plurality of films 14, a photoresist layer 16 and an edge exposure area 12. The edge exposure area 12 has a width 12a between the edge of the wafer 10 and the edge of the photoresist layer 16.

The light source 122 is positioned over the side of the wafer 10 supported by the rotation chuck 110 and generates a light beam along a direction in parallel with the top surface of the wafer 10. The beam expansion member 124 expands the cross-sectional area of the light beam generated from the light source 122. When incident on the wafer 10, the expanded light beam preferably has a width larger than the width 12a of the edge exposure area 12 of the wafer 10. For example, when the width 12a of the edge exposure area 12 of the wafer 10 is about 5 mm, the expanded width of the light beam may be about 6 to 12 mm.

A light beam providing light to which the photoresist layer 16 is sensitive, e.g., in the ultraviolet range, may change the properties of the photoresist layer 16 on the wafer 10. Accordingly, the wavelength of the light beam is outside this sensitive region. For use with photoresist that is sensitive to ultraviolet light, the light beam may have a wavelength in the visible range, e.g., between about 600 to 700 nm.

The deflection member 126 is positioned at the edge portion of the wafer 10 supported by the rotation chuck 110. The expanded light beam proceeds toward the edge portion of the wafer 10 on the rotation chuck 110 after being deflected the deflection member 126. The deflection member 126 may include a half mirror that reflects a portion of the expanded light beam toward the edge portion of the wafer 10 supported by the rotation chuck 110, and transmits the other portion of the expanded light beam. The expanded light beam reflected from the deflection member 126 is vertically delivered onto the edge portion of the wafer 10.

A first portion of the light beam incident on the edge portion of the wafer 10 is reflected from the surface of the edge portion, and a second portion of the light beam is scattered by the edge portion. Remaining portions of the light beam are refracted or absorbed by the plurality of films 14 or the photoresist layer 16 formed on the wafer 10.

The deflection member 126 passes some of the light reflected from the edge portion of the wafer 10 to the detection unit 130. The deflection member 126 reflects the rest of the light reflected from the edge portion of the wafer 10 back toward the light source 122.

The detection unit 130 positioned over the deflection member 126 detects the light received from the deflection member 126 and converts it into an electrical signal. The detection unit 130 includes a detector, e.g., a charge-coupled device (CCD), which converts the intensity of the light into the electrical signal.

The processing unit 140 connected to the detection unit 130 analyzes the electrical signal to measure the reflectivity of the edge portion of the wafer 10. The processing unit 140 then compares the measured reflectivity with a reference reflectivity to calculate the width 12a of the edge exposure area 12. In particular, the processing unit 140 compares the measured reflectivity with the reference reflectivity to detect positions of the edge of the wafer 10 and the edge of the photoresist layer 16 so as to calculate the width between the edge of the wafer 10 and the edge of the photoresist layer 16. Additionally, the processing unit 140 compares the calculated width 12a of the edge exposure area 12 with a reference width in order to detect any defects in the edge exposure area 12.

The reference width may be changed in accordance with the size of the wafer 10. The reference width may be set in order to include as many different semiconductor chips from the wafer 10 as possible. The reference reflectivity indicates a reflectivity corresponding to the reference width, and may be obtained by performing the process for inspecting the edge exposure area 12 over a plurality of standard wafers.

The reflectivity varies in accordance with the films 14 and the photoresist layer 16 formed on the wafer 10, and each of the films 14 and the photoresist layer 16 has an intrinsic refractive index and an absorption rate. Accordingly, the width 12a of the edge exposure area 12 calculated from the reflectivity of the light reflected from the edge portion of the wafer 10 is highly reliable.

The image processor 150 connected to the detection unit 130 converts the electrical signal transmitted from the detection unit 130 into an image signal, and then transmits the image signal to the display unit 160. The display unit 160 displays the image of the edge portion of the wafer 10 in accordance with the image signal.

The apparatus for inspecting the edge exposure area 100 may further include additional conventional devices, the illustration of which is not believed necessary here. Such additional devices may include memory for storing the image signal, a pre-aligner for aligning the wafer 10 before the wafer 10 is positioned on the rotation chuck 110, an aligner for aligning the wafer 10 positioned on the rotation chuck 110, an attenuator for adjusting the power of the light beam, and an optical isolator (not shown) preventing light reflected by the deflection member 126 from reaching the light source 122.

Figure 2:
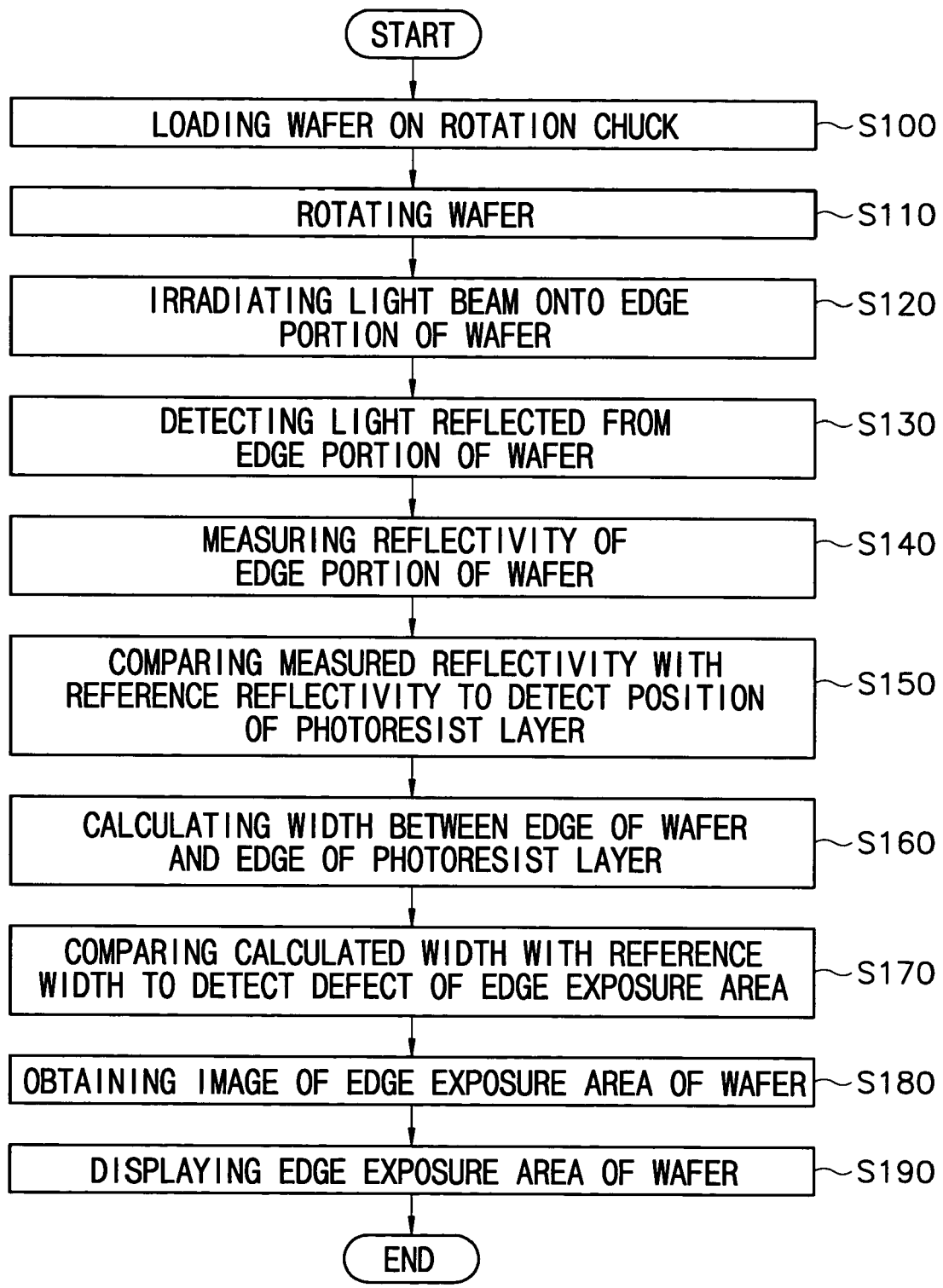
FIG. 2 is a flow chart illustrating a method for inspecting the edge exposure area using the apparatus in FIG. 1.
Figure 3:
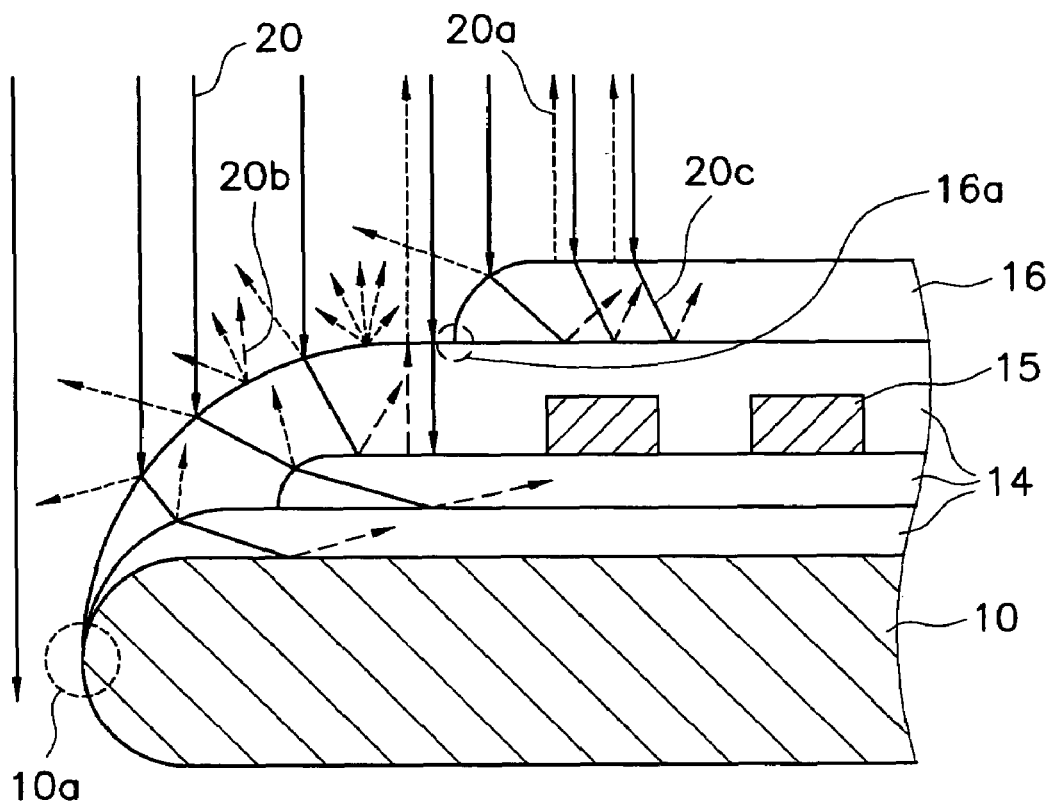
FIG. 3 is an enlarged cross-sectional view of the wafer illustrating the method for inspecting the edge exposure area.
Figure 4:
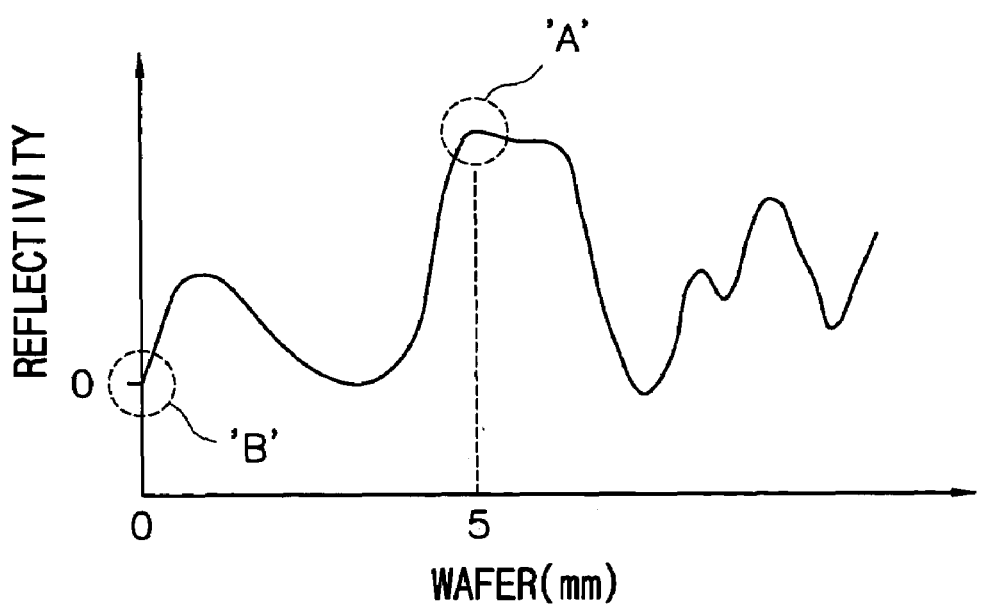
FIG. 4 is a graph illustrating a reflectivity measured using a processing unit according to one embodiment of the present invention.

FIG. 2 is a flow chart illustrating the method for inspecting the edge exposure area using the apparatus shown in FIG. 1. FIG. 3 is an enlarged cross-sectional view of the wafer illustrating the method for inspecting the edge exposure area. FIG. 4 is a graph illustrating the reflectivity measured using the processing unit.

Referring to FIGS. 1-4, the wafer 10 is horizontally loaded on the rotation chuck 110 in step of S100. The wafer 10 supported by the rotation chuck 110 is aligned using an aligner (not shown) and a lifting member (not shown). The center of the wafer 10 is made to correspond with the central line of a rotational axis 112 by the aligner and the lifting member. As can be seen in FIG. 3, the films 14, patterns 15 and the photoresist layer 16 are formed on the wafer 10.

The rotation chuck 110 fixes the wafer 10 using vacuum. The wafer 10 positioned on the rotation chuck 110 is rotated by a rotational force transferred from the rotational axis 112 in step S110.

The optical unit 120 supplies the light beam onto the edge portion of the wafer 10 rotated by the rotation chuck 110 in step S120. More particularly, the light source 122 generates the light beam in a direction parallel with the top surface of the wafer 10, and the beam expansion member 124 expands a cross-sectional area of the light beam generated from the light source 122. The deflection member 126 deflects the expanded light beam in order to illuminate the edge portion of the wafer 10 with the expanded light beam. The deflection member 126 reflects one portion of the expanded light beam toward the edge portion of the wafer 10, and transmits the other portion of the expanded light beam. As discussed above, the wavelength of the light beam may be between about 600 to about 700 nm, and the width of the expanded light beam may be between about 6 to about 12 mm.

In step S130, the light reflected from the edge portion of the wafer 10 is detected. More particularly, the detection unit 130 detects the light reflected from the edge portion of the wafer 10 and directed onto the detection unit 130 by the deflection member 126. The deflection member 126 reflects the remainder of the light reflected from the edge portion of the wafer 10 back toward the light source 122. The detection unit 130 converts the detected portion of the light reflected from the edge portion of the wafer 10 into an electrical signal, and transmits the electrical signal to the processing unit 140 and the image processor 150.

The processing unit 140 measures the reflectivity of the edge portion of the wafer 10 using the detected light in step S140. The processing unit 140 analyzes the electrical signal transmitted from the detection unit 130 to measure the reflectivity of the edge portion.

The processing unit 140 compares the measured reflectivity with the reference reflectivity to detect a position of an edge 16a of the photoresist layer 16 in step S150.

The processing unit 140 calculates the width 12a between the edge 10a of the wafer 10 and the edge 16a of the photoresist layer 16 in step S160. More particularly, a light beam 20 incident on the edge portion of the wafer interacts with the edge portion in a number of manners. A first portion 20a of the light beam 20 is reflected from a surface of the edge portion and the surface of the photoresist layer 16. A second portion 20b of the light beam 20 is scattered. Another portion 20c of the light beam 20 is refracted or absorbed in the films 14 or the photoresist layer 16 formed on the wafer 10. The photoresist layer 16 has a higher light absorption rate, and hence a lower reflectivity, than that of the films 14. Thus, where the photoresist layer 16 is formed, less light is reflected than that from where the films 14 are formed. Accordingly, as shown in FIG. 4, the reflectivity of the light reflected from the edge portion of the wafer 10 has a peak 'A' in intensity corresponding to the edge 16a of the photoresist layer 16. The reflectivity of the light reflected from the edge 10a of the wafer 10 corresponding to the edge 10a of the wafer 10, here indicated as zero, is 'B'. The reflectivity has a plurality of peaks due to the films 14 formed on the wafer 10. Among the peaks, the processing unit 140 selects a peak value corresponding to the reference reflectivity, and calculates the width between the position corresponding to the edge 10a of the wafer 10 and the position corresponding to the selected peak value.

However, the peak corresponding to the edge 16a of the photoresist layer 16 may not be generated in accordance with the properties of the films 14 formed on the wafer 10. When the peak value corresponding to the reference reflectivity is not apparent, the width 12a of the edge exposure area 12 may be calculated from the position where the reflectivity substantially identical to the reference reflectivity is detected.

The processing unit 140 compares the calculated width 12a of the edge exposure area 12 with the reference width to detect any defects of the edge exposure area 12 in step S170. When the difference between the detected width 12a of the edge exposure area 12 and the reference width is larger than the predetermined allowable value, the processing unit 140 stores information regarding the position of this defective edge and the difference, which is in turn display by the display unit 160.

The image processor 150 obtains the image of the edge portion of the wafer 10 using the light detected by the detection unit 130 in step S180. In other words, the image processor 150 converts the electrical signal transmitted from the detection unit 130 into the image signal to obtain the image of the edge portion of the wafer 10.

The display unit 160 displays the image of the edge portion of the wafer 10 in step of S190. Additionally, the display unit 160 may display the reflectivity measured in the processing unit 140, the position of the edge 16a of the photoresist layer 16, and the width 12a of the edge exposure area 12.

According to the present invention, the reflectivity of the light reflected from the edge portion of the wafer is measured, and the measured reflectivity is compared with the reference reflectivity to calculate the width of the wafer edge exposure area. The measured reflectivity has a particular value depending on properties of the films and the photoresist layer formed on the wafer. Thus, the reliability of the process for inspecting the wafer edge exposure area is improved.

Additionally, the process for inspecting the edge exposure area is automatically performed using the above apparatus for inspecting the edge exposure area to prevent contamination of the wafer.

Exemplary embodiments of the present invention have been disclosed herein, and although specific terms are employed, they are used and interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A method for inspecting an edge exposure area of a wafer between an edge of a photoresist layer formed on the wafer and an edge of the wafer, comprising:
    irradiating light onto an edge portion of the wafer;
    measuring a reflectivity of the light reflected from the edge portion of the wafer; and
    selecting a peak value of the measured reflectivity corresponding to a reference reflectivity, wherein the selected peak value of the measured reflectivity corresponds to the edge of the photoresist layer;
    calculating a width of the edge exposure area between a position corresponding to the selected peak value and a position of the edge of the wafer;
    obtaining an image of the edge portion of the wafer using the reflected light; and
    displaying at least one of the image, the measured reflectivity, the position of the edge of the photoresist layer and the width of the edge exposure area.

2. The method as claimed in claim 1, wherein the light is irradiated over the edge portion of the wafer by:
    rotating the wafer; and
    irradiating the light onto the edge portion of the rotating wafer.

3. The method as claimed in claim 1, wherein the irradiating further includes providing the light vertically incident onto the edge portion of the wafer.

4. The method as claimed in claim 1, further comprising comparing the calculated width of the edge exposure area with a reference width to detect a defect of the edge exposure area of the wafer.

5. The method as claimed in claim 1, further comprising expanding the light such that a width of the light incident on the edge portion of the wafer is larger than the edge portion of the wafer.

6. The method as claimed in claim 1, wherein a width of the light on the edge portion of the wafer is about 6 to about 12 mm.

7. The method as claimed in claim 1, wherein the irradiating further includes providing light having a wavelength outside a wavelength range to which material in the edge portion is sensitive.

8. The method as claimed in claim 1, wherein the light irradiated onto the edge portion of the wafer has a wavelength of about 600 to about 700 nm.

9. The method as claimed in claim 1, wherein the light is irradiated over the edge portion of the wafer by:
    rotating the wafer; and
    irradiating the light onto the edge portion of the rotating wafer.

10. The method as claimed in claim 1, wherein displaying comprises displaying the image, the measured reflectivity, the position of the edge of the photoresist layer and the width of the edge exposure area.

11. An apparatus for inspecting an edge exposure area of a wafer between an edge of a photoresist layer formed on the wafer and an edge of the wafer, comprising:
    an optical unit adapted to irradiate a light beam onto an edge portion of the wafer;
    a detection unit adapted to detect a light reflected from the edge portion of the wafer;
    a processing unit adapted to measure a reflectivity of the edge portion of the wafer using the light detected in the detection unit, selecting a peak value of the measured reflectivity corresponding to a reference reflectivity, and calculating a width of the edge exposure area between a position corresponding to the selected peak value and a position of the edge of the wafer, wherein the peak value of the measured reflectivity selected by the processing unit corresponds to the edge of the photoresist layer.

12. The apparatus as claimed in claim 11, wherein a portion of the light beam is vertically irradiated onto the edge portion of the wafer.

13. The apparatus as claimed in claim 11, wherein the processing unit compares the measured width of the edge exposure area with a reference width to detect a defect of the edge exposure area of the wafer.

14. The apparatus as claimed in claim 11, further comprising a rotation chuck for rotating and supporting the wafer.

15. The apparatus as claimed in claim 11, wherein the optical unit comprises:
    a light source for generating the light beam; and a deflection member for guiding the light beam toward the edge portion of the wafer.

16. The apparatus as claimed in claim 11, wherein the detection unit includes a charge-coupled device for converting the detected light into an electrical signal.

17. The apparatus as claimed in claim 16, further comprising an image processor for converting the electrical signal into an image signal, and a display unit for displaying the image of the edge portion of the wafer based on the image signal.

18. The apparatus as claimed in claim 15, wherein the optical unit further comprises a beam expansion member for expanding a cross-sectional area of the light beam.

19. The apparatus as claimed in claim 15, wherein the deflection member comprises a half mirror positioned over the edge portion of the wafer, the half mirror reflecting a portion of the light beam generated from the light source to the edge portion of the wafer and transmitting the other portion of the light beam generated from the light source.

20. The apparatus as claimed in claim 18, wherein the cross-sectional area of the light beam incident on the wafer provided by the beam expansion member is larger than the beam expansion area.

21. The apparatus as claimed in claim 19, wherein the detection unit is positioned over the half mirror, and the light reflected form the edge portion of the wafer proceeds toward the detection unit through the half mirror.

* * * * *